United States Patent [19]

Ritter

[11] Patent Number: 4,646,377
[45] Date of Patent: Mar. 3, 1987

[54] COMBATING VAROATOSIS IN BEES

[75] Inventor: Wolfgang Ritter, Freiburg, Fed. Rep. of Germany

[73] Assignee: Bayer Aktiengesellschaft, Leverkusen, Fed. Rep. of Germany

[21] Appl. No.: 735,501

[22] Filed: May 17, 1985

[30] Foreign Application Priority Data

Jun. 4, 1984 [DE] Fed. Rep. of Germany ....... 3420751

[51] Int. Cl.$^4$ ............................................. A01K 51/00
[52] U.S. Cl. ...................................................... 6/12 M
[58] Field of Search ............................... 6/12 M, 12 R

[56] References Cited

U.S. PATENT DOCUMENTS 4,308,627 1/1982 Wallace ............................... 6/12 M

FOREIGN PATENT DOCUMENTS 2208618 9/1973 Fed. Rep. of Germany .
3225493 1/1984 Fed. Rep. of Germany ....... 6/12 R

OTHER PUBLICATIONS

Commonwealth Agricultural Bureau, 1981, Abstract 81A31243.
Commonwealth Agricultural Bureau, 1983, Abstract 83238811.

Primary Examiner—Robert P. Swiatek
Attorney, Agent, or Firm—Sprung Horn Kramer & Woods

[57] ABSTRACT

A process for combating Varoa Jacobsoni on bees, comprising applying to the bees or their habitat an amount effective therefor of 0,0-diethyl 0-(3-chloro-4-methyl-7-coumarinyl) thionophosphate.

3 Claims, No Drawings

COMBATING VAROATOSIS IN BEES

The present invention relates to a new process for combating Varoa Jacobsoni on bees, and to varoatosis agents containing O,O-diethyl O-(3-chloro-4-methyl-7-coumarinyl)thionophosphate(coumaphos).

Varoatosis is caused by the mite Varoa Jacobsoni which, in the adult form, parasitises bees, drones and queen bees and, in its preimaginal development forms, parasitises the larvae of bees and drones and the pupae. The damage which is caused directly by the mite is accompanied by a general debilitation of the bees, which makes them susceptible to attack by viruses and bacteria.

This parasitism is new in apiculture and has already reached a panzootic form. Varoatosis produces great damage in apiculture due to the acute debilitation and high mortality of the bee colony. Moreover, the direct products of apiculture, such as honey, wax, royal jelly and bee venom, are affected by this. However, because of the reduction in pollination of the entomophilic agricultural crops, it also adversely affects the indirect use of the bees, which exceeds the direct production by the bees by 10-15 times.

The methods known hitherto for combating varoatosis in bees have entailed the bee colony being treated with smoke or dusted with chemical active compounds.

The method of heat treatment and the mechanical elimination of the uncapped drone brood are also known.

The disadvantage of the known methods is the great manual effort in applying them and the disturbance of the bee colony which is brought about by the treatment.

The present invention relates to a process for combating varoatosis, which is characterized in that 10-50 mg of O,O-diethyl O-(3-chloro-4-methyl-7-coumarinyl)thionophosphate(coumaphos) per treatment and per bee colony are distributed in the form of an aqueous suspension or emulsion, which contains 100-1,000 ppm of active compound, by pouring on, dropwise application to, or spraying on.

The process of treatment according to the invention is carried out two to three times at intervals of 4-20 days, preferably at intervals of 1-2 weeks, during the low brood period, for example during the overwintering period or the resting period.

For one treatment, 30-60 ml of a dilute aqueous suspension or emulsion of coumaphos are distributed per bee colony. 50 ml are preferred. The distribution is carried out by simply pouring on, dropwise application to or spraying on.

This entails 10-50 mg, preferably 15-30 mg, of of coumaphos being applied to each bee colony.

The concentration of active compound in the dilute aqueous suspension or emulsion is 100-1,000 ppm. It is preferably 200-700 ppm, and particularly preferably about 500 ppm.

An emulsion or suspension concentrate with a concentration of active compound of 0.1-20%, preferably 10-20%, particularly preferably 16%, is used to prepare the solution which is ready for use.

These formulations are prepared in a known manner, for example by mixing the active compound with extenders, that is to say liquid solvents, where appropriate using surface-active agents, that is to say emulsifiers and/or dispersing agents. In the case where water is used as the extender, it is also possible to use, for example, organic solvents as auxiliary solvents. The liquid solvents which are essentially suitable are: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol, and their ethers and esters, ketones, such as acetone, methyl ethyl ketone, methyl isobutyl ketone or cyclohexanone, highly polar solvents, such as dimethylformamide and dimethyl sulphoxide, and water; suitable emulsifiers are: for example non-ionic and anionic emulsifiers, such as polyoxyethylene fatty acid esters, polyoxyethylene fatty alcohol ethers, for example alkylarylpolyglycol ethers, alkylsulphonates, alkyl sulphates, arylsulphonates and protein hydrolyzates; suitable dispersing agents are: for example lignin sulphite waste liquors and methylcellulose.

It is unnecessary to wet every bee and its entire living space with the solution of active compound by atomization, spraying or smoking.

Surprisingly, coumaphos has a systemic effect both on the bees and on the larval stages of the bees.

That is to say the active compound is conveyed by being transported in the body fluid to the mite which is imbibing from the bee.

Due to this mode of action, it is unnecessary to wet all the livestock in order thus to make contact with the mites which are imbibing from them. This systemic action in bees was surprising because coumaphos shows no systemic action when used to combat ectoparasites in warmblooded animals.

Examples of formulations from which the solutions which are ready for use can be prepared by dilution with water are indicated below:

EXAMPLE 1

Coumaphos: 20 g
Emulsifier Toximul R ® (mixture of Ca alkylbenzenesulphonate and non-ionic emulsifiers and methanol with a hydrophilic/lipophilic balance, HLB value: 10): 7 g
Emulsifier Toximul S ® (mixture of Ca alkylbenzenesulphonate and non-ionic emulsifier, methanol with hydrophilic/lipophilic balance, HLB value: 10): 5 g
Solvesso 200 ® (alkylnaphthalene mixture from high-boiling petroleum fractions): ad 100 ml

EXAMPLE 2

Coumaphos: 16 g
Emulsifier 368 ® alkylarylpolyglycol ethers (molecular weight about 1165): 9 g
Emulsifier NP 10 ® nonylphenyl polyglycol ethers: 9 g
Dimethylformamide: 10 g
Solvesso 200 : ad 100 ml

EXAMPLE 3

Coumaphos: 5 g
Emulsifier Altox ® (mixture of polyoxyethylene ethers, polyoxyglyceride, alkylarylsulphonate—very readily soluble in water): 4 g
Emulsifier Atlox 3404 ® (mixture of polyoxyethylene alkylaryl ethers, alkylarylsulphonate—forms emulsion in water): 2 g
Emulsifier Atlox 3409 ® (mixture of non-ionic and anionic emulsifiers—soluble in water): 4 g Solvent PC 2 (high-boiling aromatic petroleum fraction): ad 100 ml

EXAMPLE 4

Coumaphos: 1 g
Emulsifier 368: 30 g
Dowanol DPM ® (dipropylene glycol methyl ether): ad 100 ml

EXAMPLE 5

Coumaphos: 2.5 g
Emulsifier 368: 10 g
Emulsifier NP 10: 10 g
Solvesso 200: 20 g
Dowanel DPM: ad 100 ml

EXAMPLE 6

Coumaphos: 2 g
Emulsifier 368: 9 g
Emulsifier NP 10: 9 g
Solvesso 200: 16 g
Dowanol DPM: 45 g
Water: ad 100 ml

EXAMPLE 7

Coumaphos: 1 g
Emulsifier 368: 10 g
Emulsifier NP 10: 10 g
Salvesso 200: 10 g
Dowanol DPM: ad 100 ml

EXAMPLE 8

Coumaphos: 2.5 g
Emulsifier Tween 80 ® (sorbitan monooleate with HLB value: 4.3): 8 g
Emulsifier Span 80 ® (sorbitan monooleate with HLB value: 15): 4 g
N-Methylpyrrolidone: ad 100 ml

EXAMPLE 9

Coumaphos: 1 g
Cremophor HS 15 ® (polyoxyethylene 600 hydroxystearate): 20 g
Chlorobenzene: ad 100 ml

EXAMPLE 10

Coumaphos: 1 g
Emulsifier W ® (alkylarylpolyglycol ether, molecular weight about 853): 90 g
Dimethylisosorbitol: ad 100 ml The excellent effect which can be achieved with the method of treatment according to the invention is evident from the experiments which follow:

EXAMPLE

Bee colonies of the indicated sizes are treated by dropwise application of 50 ml of an aqueous emulsion of coumaphos. 5 ml of the emulsion are introduced dropwise into each gap between the honeycombs. The concentration of the emulsion in this experiment is 30 ppm, 60 ppm or 90 ppm.

Three treatments at intervals of 5 days are carried out. The number of killed mites and bees is determined after each treatment.

The bee colony was sacrificed after completion of the treatment. The bees are counted and the mites which are still present are washed out from the bees.

The total number of mites which was originally present was then determined. Thereafter, the level of bees and mite mortality which took place after each treatment was calculated.

The results of the experiments comparing with a commercially available agent are shown in the table below. The commercially available agent, with the tradename Folbex VA ® is used as a smoke, in accordance with instructions, in these experiments. The active compound contained in the commercially available agent is isopropyl 4,4'-dibromobenziate.

TABLE

| Agent | Mite mortality in % after treatment | | | Bee mortality in % after treatment | | |
|---|---|---|---|---|---|---|
| | 1 | 2 | 3 | 1 | 2 | 3 |
| Folbex VA according to the invention dose | 40.4 | 67.0 | | 0.1 | 0.1 | |
| 30 ppm | 78.2 | 93.3 | 98.6 | 0.4 | 0.7 | 1.5 |
| 60 ppm | 91 | 97.5 | 99 | 0.5 | 1.0 | 2.2 |
| 90 ppm | 90.7 | 97 | 100 | 0.5 | 1.0 | 1.0 |

It will be understood that the specification and examples are illustrative but not limitative of the present invention and that other embodiments within the spirit and scope of the invention will suggest themselves to those skilled in the art.

What is claimed is:

1. A process for combating Varoa Jacobsoni on bees, comprising applying to the bees or their habitat an amount effective therefor of O,O-diethyl-O-(3-chloro-4-methyl-7-coumarinyl)thionophosphate.

2. A process according to claim 1, wherein the thionophosphate is applied as an aqueous suspension or emulsion containing 100 to 1000 ppm of the O,O-diethyl-O-(3-choro-4-methyl-7-coumarinyl)thionophosphate.

3. A process according to claim 2, wherein the suspension or emulsion is applied to a bee colony in the amount of 10 to 50 mg of the O,O-diethyl-O-(3-chloro-4-methyl-7 -coumarinyl)thionophosphate.

* * * * *